United States Patent [19]

Steinmetzer

[11] Patent Number: 5,369,122
[45] Date of Patent: Nov. 29, 1994

[54] PROCESS FOR MANUFACTURING A HUMECTANT

[75] Inventor: Walter Steinmetzer, Süpplingen, Germany

[73] Assignee: Amino GmbH, Frellstadt, Germany

[21] Appl. No.: 855,724

[22] Filed: Mar. 20, 1992

[30] Foreign Application Priority Data

Mar. 28, 1991 [EP] European Pat. Off. ........ 91104968.2

[51] Int. Cl.$^5$ ..................... A61K 31/40; C07D 207/28
[52] U.S. Cl. ..................... 514/423; 514/557;
252/8.8; 426/321; 426/334; 548/531; 548/534; 560/179
[58] Field of Search ........ 548/535, 531, 534; 560/179; 514/423, 557; 252/8.8; 426/321, 334

[56] References Cited

U.S. PATENT DOCUMENTS

| | | | |
|---|---|---|---|
| 2,742,482 | 4/1956 | Heegaard | 548/534 |
| 2,785,179 | 3/1957 | Julsingha | 548/534 |
| 2,785,180 | 3/1957 | Julsingha | 548/534 |
| 3,153,049 | 10/1964 | Melis et al. | 548/534 |
| 3,884,714 | 5/1975 | Schneider | 127/46.2 |
| 3,957,971 | 5/1976 | Oleniacz | 424/70 |
| 4,762,522 | 8/1988 | Maue | 252/8.57 |
| 4,946,968 | 8/1990 | Krimmer et al. | 548/534 |

FOREIGN PATENT DOCUMENTS 2232093 8/1977 Germany.

OTHER PUBLICATIONS

Technologie des Zuckers, pp. 520, 530 (1955).
Technologie des Zuckers, pp. 977, 1008, 1009 (1968).
Beet-Sugar Technology, R. A. McGinnis, 2nd Ed, pp. 598–609 (date not available).
Chem. Abstracts 83 (14) 117539 N (1974).
Die Verwertung der Nichtzuckerstoffe der Zuckerrubenmelasse, Steinmetzer, Zucker Industrie, 116 (1991), pp. 3–12.
"Beet Sugar Technology", 2nd Edition, pp. 599–608.

*Primary Examiner*—C. Warren Ivy
*Assistant Examiner*—A. A. Owens
*Attorney, Agent, or Firm*—Herbert Dubno; Jonathan Myers

[57] ABSTRACT

In a process for manufacturing a humectant with a chemical structure similar to that of natural moisture regulators, residual molasses from sugar beet molasses are treated and the organic acids contained, in particular L-2-pyrrolidone-5-carboxlyic acid and lactic acid, are obtained and then neutralized and concentrated to form a humectant.

15 Claims, No Drawings

PROCESS FOR MANUFACTURING A HUMECTANT

BACKGROUND OF THE INVENTION

Humectants or moisture stabilizers are used in the manufacture of foodstuffs and industrial products in order to prevent the products drying out. Another principal area of application for these moisture stabilizers is skin care products for keeping the skin moist and supple. The surface of the human skin, the epidermis, contains natural moisture regulators. These moisture regulators—known as Natural Moisturising Factors NMF—are described in detail in the relevant literature, e.g. Römpp Chemie Lexikon 9th edition (1990) Vol.2, p. 1347, and consists of 40% free amino acids, 12% L-2-pyrrolidone-5-carboxylic acid, 12% lactate, 7% urea, 1.5% uric acid, glucosamine, keratin, ammonium, sodium, potassium, magnesium and calcium citrates, formates, phosphates and chlorides.

In addition to the moisture-regulating effect, the organic acids also exercise a protective function for the skin, since they form a natural acidic mantle. These natural humectant substances are dissolved out by soaps or other surfactants, and the result is drying out and scaling off of the skin. These natural moisture regulators are meant to be replaced in skin care products by synthetic humectants such as glycols, glycerine or hydrolysates of keratin or collagen-containing substances.

It would be desirable, however, at least as an alternative to the synthetic humectants, to obtain also natural humectants or possibilities possessing the identical or a similar chemical composition to the natural humectants.

In an article by Klaus Hoffmann, "Lactil—a new humectant complex", in: Seifen-Ole-Fette-Wachs 103 (1977), 7, the importance of 2-pyrrolidone-5-carboxylic acid as a natural substance peculiar to the skin is emphasized and proposed for use in hydroregulative cosmetics. A problem area is still the obtaining of suitable humectants from natural products.

SUMMARY OF THE INVENTION

The aim of the invention is therefore to provide a process for manufacturing a humectant with which possibilities chemically similar to the natural moisture regulators are provided.

According to the present invention there is provided a process for manufacturing a humectant wherein sugar-free or partially desugarized residual molasses from sugar beet molasses is subjected to a treatment, the molasses containing potassium salts of organic acids, in particular of L-2-pyrrolidone-5-carboxylic acid and of lactic acid, the treatment converting the salts into the acids and by-products, the by-products are separated from the acids, and the acids are neutralized, decolorized and concentrated to form a humectant.

DESCRIPTION OF THE PREFERRED EMBODIMENTS

Basically the present invention provides that sugar-free or partially desugarized residual molasses from sugar beet molasses is subjected to a treatment in which included potassium salts of organic-acids, in particular of L-2-pyrrolidone-5-carboxylic acid and of lactic acid, are converted into the free acids, the by-products are separated from the free acids, which are neutralized, decolorized and concentrated to form a humectant.

This novel process makes it possible to obtain natural moisture regulators from the non-sugar substances of the sugar beet molasses, i.e. from as it were a waste product in sugar manufacture.

The invention is moreover based on the discovery that the sugar beet molasses contains the natural moisture stabilizers L-2-pyrrolidone-5-carboxylic acid, lactic acid, citric acid and other organic acids as well as free amino acids, namely in the form of potassium salts and in a ratio that approximates to the desired natural moisture regulators.

By means of the process steps according to the invention it is possible to isolate the natural moisture regulators out of the sugar beet molasses.

The sugar beet molasses is a syrup with such a low purity that during the further concentrating no more sugar crystallizes out. The sugar beet molasses has a dry matter content of approx. 78% and contains, in addition to 48% saccarose, also 30% organic and inorganic non-sugar substances. These are in the main the potassium and sodium salts of various organic acids as well as free amino acids, betaine and other organic substances.

Some organic non-sugar substances of the sugar beet molasses are already used commercially. Thus by means of acid or alkaline hydrolysis the L-pyrrolidonecarboxylic acid may be converted into L-glutamic acid and in this way monosodium glutamate be obtained, cf. Ferdinand Schneider, Technologie des Zuckers (1968), pp. 977, 1008–1009; R. A. McGinnis, Beet Sugar Technology (1971), pp. 599–608.

In a recent article by Walter Steinmetzer, the recycling of the non-sugar substances of sugar molasses, in: Zuckerindustrie (1991), pp. 30–39, the isolation of various amino acids and betaine by means of chromatographic methods from sugar beet molasses is described.

In contrast to the known recycling of non-sugar substances, however, according to the present new process the whole complex of the organic acids is isolated and used for the manufacture of a natural humectant.

The sugar beet molasses serves as a raw material for various biotechnological processes, such as the obtaining of ethanol, citric acid, gluconic acid, glutamic acid and baker's yeast. For the isolation of sacchrarose from the sugar beet molasses, various chemical and chromatograph methods are available. In all these processes residual molasses remain behind, which contain the non-sugar substances in enriched form. The residual molasses, also called vinasses or molasses slop, are the raw materials for the present invention. Preferred as raw material, however, are the residual molasses obtained during the chromatographic separation of the sugar beet molasses. During the chromatographic separation according to the ion exclusion method the polar non-sugar substances are obtained in the first fraction, followed by a saccharose fraction and a betaine fraction. In the first non-sugar substance fraction the potash salts of the pyrrolidone carboxylic acid, lactic acid and other organic acids, in addition to some amino acids such as serine and threonin, are enriched. The two amino acids are likewise of importance for the obtaining of the main function as a moisture regulator. Further constituents of the partially desugarized molasses are the molasses pigments, such as melanin, melanoidin and caramel pigments, and residual portions of saccharose, raffinose and monosaccharides.

Three alternative possibilities for carrying out the process have proved particularly promising.

In the first alternative one proceeds in such a way that the residual molasses is acidified to a pH value of at least 3.0, in particular of 1.5 to 2.0, and with an organic solvent the organic acids, in particular L-2-pyrrolidone-5-carboxylic acid and lactic acid, are extracted, neutralized and concentrated to form a humectant.

The process has proved to be particularly inexpensive. The use of sulphuric acid for the acidification is preferred with $K_2SO_4$ being formed as by product.

With an organic solvent, particularly preferably with butanol or isobutanol, the organic acids forming, in particular $H^+$—$PCS^-$, are then obtained. The organic acids present as potassium salts may not be separated directly from the residual molasses, but they may certainly be so as free organic acids, in particular from butanol and isobutanol.

In a second alternative one proceeds in such a way that the residual molasses is passed through a cation exchanger and the potassium ions are bonded to the latter and, thereafter the formed free organic acids forming are extracted.

In the cation exchanger method, the hydrogen cation form is particularly preferred. The potassium ions of the potassium salts are bonded to the exchanger, whereby the organic acids in their free form are formed and may once again be extracted, in particular with butanol or isobutanol.

Besides potassium ions troublesome pigments are also adsorbed by the exchanger. Thus, the procedure provides especially good yields and degrees of purity.

A third alternative consists of passing the residual molasses through a cation exchanger wherein the potassium ions are bonded to the exchanger. Afterward the mixture remaining behind is passed through an anion exchanger and the free organic acids formed are bonded to the latter. The mixture then remaining behind is removed and the organic acids, in particular L-2-pyrrolidone-5-carboxylic acid and lactic acid, are eluted from the anion exchanger, neutralized and concentrated to form a humectant.

The third procedure has proved to be the best method. Whereas to start with, as in the second alternative, a cation exchanger preferably in H form is used, the organic acids are now however not extracted directly from the remaining mixture behind. Instead, this mixture is passed through an anion exchanger, and the free organic acids which have just formed are now bonded to the latter. All the substances still remaining behind now in the mixture are by-products and may run off. The organic acids, in particular the L-2-pyrrolidone-5-carboxylic acid and the lactic acid, may now in turn be separated from the anion exchanger, preferably by sulphuric acid. They are thus directly available and may be neutralized and concentrated to form a humectant.

In certain circumstances it is likewise also necessary with the third alternative procedure to undertake an extraction from the end product, which would once again preferably be carried out with butanol or isobutanol. Extraction depends somewhat on the nature of the residual molasses used as starting material for the process. Particularly if the phases of the residual molasses exist in relatively pure form, however, tests have shown that an extraction is not necessary if the process variant is chosen.

The process may be carried out particularly well with an extraction of the free organic acids by means of butanol or isobutanol. In the case of the acidification of a residual molasses to a pH value of, in particular, 1.5 to 2.0 the L-2-pyrrolidone-5-carboxylic acid, the lactic acid and other organic acids are separated from the sugar and the potash salt.

According to the invention, during such an extraction of the organic acids a part of the molasses pigments also passes into the organic phase in certain circumstances. The solutions of the organic acids are therefore dark coloured after distilling off the solvent, and there are contained in the aqueous phase the remaining pigments together with potash salt and sugar.

For a further improvement of the process according to the invention, a three-stage embodiment has therefore been developed, which will be described below. Concurrent with this description there additionally follows a discussion of preferred possibilities of the process, since the various steps, at least in part, may also be carried out independently of one another. For example sulphuric acid in particular has proved to be suitable for the acidification of the residual molasses.

In the first separation stage the residual molasses is treated with a strongly acid, preferably macroporous cation exchanger in H form. The residual molasses with approx. 10% dry matter is moreover passed through the cation exchanger at a rate of 5–10 bed volumes per hour, until a pH value of 5–6 is reached in the outlet. In so doing, all the hydrogen ions are completely replaced by potassium ions, and the exchanger is then eluted with 4% sodium hydroxide solution and the pigments dissolved. After the rewashing with water, the exchanger is again regenerated with sulphuric acid. The following fractions are collected in the outlet of the cation exchanger:

Fraction 1 up to pH 2.5 for the obtaining of the organic acids,

Fraction 2 from pH 2.5 to 6.0 recycling to the next exchanger cycle,

Fraction 3 from pH 6.0 to 9.0 pigment fraction,

Fraction 4 potassium sulphate solution for the manufacture of potassium sulphate, Fraction 5 sulphuric acid for the pre-regeneration for the next cycle.

Optionally, the first fraction may now be extracted after concentrating with butanol or isobutanol. In so doing the sugar remains behind with a part of the pigments and non-extractable substances of the aqueous phase, and the organic acids in the butanol phase are after neutralization extracted with water and isobutanol is returned into the process. The aqueous phase of the salts of organic acids is concentrated and a humectant obtained.

Preferably, however, the first fraction from the cation exchanger is treated in the next separation stage, with a weakly basic preferably macroporous anion exchanger. The organic acids are in so doing bonded jointly with the pigments to the exchanger, and in the outlet of the anion exchanger a decolorized salt-free sugar solution is obtained. On the reaching of a pH value of 6.0 in the outlet, the anion exchanger is sweetened and the organic acids eluted with dilute sulphuric acid or hydrochloric acid, rewashed with water, and after this the anion exchanger is then regenerated with ammonia.

By means of the elution, according to the invention, of the organic acids from the anion exchanger with dilute inorganic acids the organic acids are obtained in free form and the active groups of the anion exchanger are saturated with sulphate and chloride ions without the adsorbed pigments being dissolved. A surprising and unforeseeable effect results in the organic acids being obtained in a light-coloured solution and a subsequent extraction with an organic solvent being superfluous in the case of a few residual molasses.

In addition to the obtaining of pure sugar solutions and pure solutions of the organic acids there is obtained in the separation stage a concentrated pigment solution during the regeneration with ammonia. During the elution of the organic acids from the anion exchanger by means of dilute sulphuric acid, the surplus sulphuric acid is neutralized by the addition of calcium carbonate or calcium hydroxide and after the evaporation filtered off as calcium sulphate. In a further purification stage, the solutions may also be subjected to a butanol extraction. As will be explained in the examples which now follow, it is however possible after each separation stage for the extraction of the organic acids to be carried out at a pH value of at least 3.0, in particular from 1.5 to 2.0, with the organic solvent.

A fourth possibility for the separation according to the invention of the hydroactive organic acids from the residual molasses consists in the application of electrodialysis. The known method of electrodialysis is a substance separation process in which, under the force of an electric field with the assistance of ion-selective membranes, the electrically charged particles are removed from a solution. If the separation process is implemented, use is preferably made of fractions of the partially desugarized molasses from the chromatographic separation process of the sugar beet molasses processing. In so doing the polar potassium salts of the organic acids are separated by means of the semi-permeable cation and anion exchanger membranes from the non-polar sugar and pigment portions. The potassium salts of the hydroactive acids, pyrrolidone and lactic acid, may be concentrated and used directly as humectants. Preferably, however, the potassium salts are converted by means of a strongly acid cation exchanger into the free acids, decolorized with activated carbon and after neutralization with sodium hydroxide solution or sodium carbonate concentrated to form a humectant. The desalinated non-polar substances, such as sugar and pigments, together with amino acids, produce after the concentrating a valuable feedstuff.

From the application of the separation processes described here there follows also the possibility of manufacturing various derivatives and modifications of the humectant. Thus, by means e.g. of acid or alkaline hydrolysis, a part of the pyrrolidone-carboxylic acid may be converted into glutamic acid, and in this way flavour-selective humectants for the food industry are obtained. Other possibilities consist in the esterification or acetylation of the organic acids according to known methods. Particularly simple is the obtaining of the butyl esters during the described extraction of the organic acids by means of butanol. The various derivatives may be used in turn as hydroactive plasticizers in the plastics industry or as finishers in the textile industry.

There will now be listed below, as concrete possibilities for the implementation of the process according to the invention, three examples with the humectants obtained:

EXAMPLE 1

1000 g of thick slop with 70% dry matter from ethanol manufacture are adjusted with 38 g of 5 molar sulphuric acid to a pH value of 1.7 and heated for 60 min. at 120° C. in an autoclave in order to destroy pigments, and after the cooling approx. 300 g of a mixture of potassium sulphate and humic substances are filtered off. The acid filtered solution is then extracted twice with 500 ml isobutanol, the butanol phase is adjusted with 1 molar sodium hydroxide solution to a pH value of 6 to 7, the aqueous phase containing the sodium salts of the organic acids is separated and after decolorization by means of activated carbon or adsorber resins the solution is concentrated, and approx. 220 g of a humectant with approx. 50% dry matter is obtained.

EXAMPLE 2

1 l of a macroporous strongly acid cation exchanger is decanted into a 50 mm diameter glass column and, as usual regenerated with sulphuric acid, rewashed and back-flushed. Onto the separating column prepared in this way, a partially desugarized molasses from the molasses separation is fed by means of ion exclusion chromatography with approx. 10% dry matter and individual 1 l fractions are withdrawn at the outlet of the column. The first 4 l from pH value 1.0 to 2.5 are used to obtain the organic acids and the next 4 l from pH 2.5 to 6.0 are fed again during the next separation cycle. After this the column is rewashed with 1.5 l water and then the pigments are eluted by means of 500 ml of 1 molar sodium hydroxide solution, rewashed again with water and regenerated with 1 l of 1 molar sulphuric acid. During the regeneration 2 fractions are likewise withdrawn. The first fraction contains mainly potassium sulphate and the second fraction mainly free sulphuric acid. The second fraction is used for the pre-regeneration during the next cycle. The first fraction from the cation exchanger containing the organic acids is concentrated and extracted with twice the amount of butanol. The butanol phase containing the free organic acids is neutralized with 1 molar sodium hydroxide solution, butanol is separated and returned again into the extraction process. The aqueous phase containing the salts of the organic acids is concentrated to approx. 250 g and a humectant containing approx. 38% pyrrolidone-carboxylic acid and approx. 25% lactic acid is obtained in the dry matter.

EXAMPLE 3

1 liter of macroporous weakly basic anion exchanger is decanted into a 50 mm diameter glass column and, as usual, regenerated with ammonia, rewashed and back-flushed. There are then passed through this anion exchanger 4 l outlet from the cation exchanger with pH 1.0 to 2.5 at a rate of 5 bed volumes per hour. At the outlet of the exchanger a sugar solution with 4% dry matter and a pH value of 7.0 to 7.5 is withdrawn. On the reaching of a pH value of 6.0 in the outlet, the exchanger is washed with 1.5 l water and the organic acids are eluted with 0.5 l of 1 molar sulphuric acid and then rewashed with 1.5 l water. After the washing the anion exchanger is regenerated with 1 l of 2 molar ammonia solution, rewashed with water and back-flushed. The acid eluate from the anion exchanger containing the organic acids and some free sulphuric acid is adjusted with calcium carbonate to a pH value of 2.0, concentrated and after neutralization with sodium hydroxide solution the calcium sulphate which has crystallized out is filtered off. Approx. 300 g of a humectant are obtained.

The obtained humectant has the following composition:

| Analytical values for 100% dry matter | |
|---|---|
| Sodium-pyrrolidone carboxylate | approx. 35% |
| Sodium lactate | approx. 35% |
| Sodium citrate } | |
| Sodium malate } | |
| Sodium acetate } | approx. 25% |
| Sodium formate } | |
| Mineral salts and other substances | approx. 5% |

EXAMPLE 4

1000 g of partially desugarized molasses with approx. 10% dry matter are desalinated at 12 Volt and 2 Amp. for a period of 6 hours at 20° C. in an electrodialysis apparatus, and 650 g of desalinated solution and 350 g of concentrate (humectant) with the following composition are obtained:

| | desalinated solution | humectant |
|---|---|---|
| Crude ash i. d. m. | 12% | 65% |
| Saccharose i. d. m. | 56% | 2% |
| organic acids i. d. m. | 14% | 33% |
| amino acids and pigments i. d. m. | 14% | 0% |

The electrodialysis equipment used consists of 6 cation exchanger membranes 128×62 mm, 6 anion exchanger membranes 128×62 mm, cell thickness 2 mm, cell volume and electrode flushing with 2.5% sodium sulphate solution.

It will be understood that the above description of the present invention is susceptible to various modifications, changes and adaptations.

What is claimed is:

1. A process for manufacturing a humectant containing neutralized, concentrated L-2-pyrrolidone-5-carboxylic acid and lactic acid, comprising:
    selecting an at least partially desugarized residual molasses from sugar beet molasses, said residual molasses containing potassium salts of L-2-pyrrolidone-5-carboxylic acid and of lactic acid and prepared by chromatographic separation of sugar beet molasses, using ion exclusion, into fractions and recovering the first fraction which contains the potassium salts of L-2-pyrrolidone-5-carboxylic acid and of lactic acid;
    converting said potassium salts into respective free acids thereof;
    separating said free acids from other components of said residual molasses or by-products of said conversion step; and
    neutralizing and concentrating said free acids to form said humectant.

2. A process according to claim 1, wherein said separation of the free acids is through a step selected from the group consisting of extraction and ion exchange.

3. A process according to claim 1, wherein said conversion of said potassium salts involves acidifying said residual molasses to a pH less than 3.0.

4. A process according to claim 3, wherein said pH ranges from 1.2 to 2.0.

5. A process according to claim 1, wherein said conversion of said potassium salts involves passing said residual molasses through a cation exchanger and said separating step includes solvent extracting of said free acids.

6. A process according to claim 1, wherein said conversion of said potassium salts involves acidifying said residual molasses with sulphuric acid.

7. A process according to claim 6, wherein subsequent to said acidification, said residual molasses is heated, cooled to allow potassium sulphate and pigment decomposition products to separate out and extracted with an organic solvent.

8. A process according to claim 1, wherein said conversion of said potassium salt involves passing said residual molasses through a cation exchanger to provide an eluate and thereafter said separation involves passing said eluate through an anion exchanger, and eluting said free acids from said anion exchanger.

9. A process according to claim 8, wherein said cation exchanger during said conversion step is strongly acidic, prior to regeneration adsorbed pigments on said exchanger are eluted with alkali metal hydroxides, and during regeneration of said exchanger with sulphuric acid a potassium sulphate solution is obtained.

10. A process according to claim 8, wherein said anion exchanger during said passage of eluate is weakly basic, and as a first fraction a sugar solution up to pH 6.0 is separated therefrom and thereafter said organic acids are eluted by means of dilute mineral acid or alkali metal hydroxides.

11. A process according to claim 8, wherein sulphuric acid is used in releasing said free acids from said anion exchanger.

12. A process according to claim 1, wherein said separating of said free acids involves extraction with butanol or isobutanol.

13. A process according to claim 1, comprising the further step of derivatizing said free acids in a procedure selected from the group consisting of hydrolysis, esterification and acetylation.

14. A process for manufacturing a humectant containing neutralized, concentrated L-2-pyrrolidone-5-carboxylic acid and lactic acid, comprising:
    selecting an at least partially desugarized residual molasses from sugar beet molasses, said residual molasses containing potassium salts of L-2-pyrrolidone-5-carboxylic acid and of lactic acid and prepared by chromatographic separation of sugar beet molasses, using ion exclusion, into fractions and recovering the first fraction which contains the potassium salts of L-2-pyrrolidone-5-carboxylic acid and of lactic acid;
    converting said potassium salts into respective free acids thereof;
    extracting said free acids from other components of the residual molasses or by-products of said conversion step with butanol or isobutanol; and
    neutralizing and concentrating said extracted free acids to form said humectant.

15. A process for manufacturing a humectant containing neutralized, concentrated L-2-pyrrolidone-5-carboxylic acid and lactic acid, comprising:
    selecting an at least partially desugarized residual molasses from sugar beet molasses, said residual molasses containing potassium salts of L-2-pyrrolidone-5-carboxylic acid and of lactic acid and prepared by chromatographic separation of sugar beet molasses, using ion exclusion, into fractions and recovering the first fraction which contains the potassium salts of L-2-pyrrolidone-5-carboxylic acid and of lactic acid as well as non-polar sugar and pigment impurities;

separating the potassium salts of 2-pyrrolidone-5-carboxylic acid and of lactic acid from the non-polar sugar and pigment impurities through electrodialysis, in which, under the force of an electric field, passage of the first fraction through semi-permeable cationic exchange and anionic exchange membranes removes the potassium salts which are electrically charged; and removing said potassium salts as a humectant or converting said potassium salts into respective free acids thereof by passing said salts through a strongly acidic cationic exchanger whereby the potassium cations are bonded thereto and a remaining eluate containing L-2-pyrrolidone-5-carboxylic acid and lactic acid is recovered; and neutralizing and concentrating said free acids to form said humectant.

* * * * *